United States Patent [19]
Fanton et al.

[11] Patent Number: 6,135,999
[45] Date of Patent: Oct. 24, 2000

[54] CONCAVE PROBE FOR ARTHROSCOPIC SURGERY

[75] Inventors: Gary S. Fanton, Portola Valley; Hugh R. Sharkey, Woodside; Daren L. Stewart, Belmont; Lee Weissman, San Jose, all of Calif.

[73] Assignee: Oratec Internationals, Inc., Menlo Park, Calif.

[21] Appl. No.: 09/022,612

[22] Filed: Feb. 12, 1998

Related U.S. Application Data

[60] Provisional application No. 60/037,782, Feb. 12, 1997.

[51] Int. Cl.$^7$ .................................................. A61B 18/14
[52] U.S. Cl. ............................... 606/45; 606/38; 606/39; 606/48
[58] Field of Search ........................... 606/41, 45, 46, 606/48–50, 38, 39

[56] References Cited

U.S. PATENT DOCUMENTS

| | | | |
|---|---|---|---|
| 2,090,923 | 8/1937 | Wappler | 128/303.15 |
| 3,178,728 | 4/1965 | Christensen | 3/1 |
| 3,579,643 | 5/1971 | Morgan | 3/1 |
| 3,776,230 | 12/1973 | Neefe | 128/260 |
| 3,856,015 | 12/1974 | Iglesias | 128/303.15 |
| 3,867,728 | 2/1975 | Substad et al. | 3/1 |

(List continued on next page.)

FOREIGN PATENT DOCUMENTS

| | | | |
|---|---|---|---|
| 0 257 116 A1 | 3/1988 | European Pat. Off. | A61N 1/36 |
| 0 274 705 A1 | 7/1988 | European Pat. Off. | A61M 23/00 |
| 0 479 482 A1 | 4/1992 | European Pat. Off. | A61B 17/39 |
| 0 521 595 A2 | 1/1993 | European Pat. Off. | A61M 25/01 |
| 0 542 412 A1 | 5/1993 | European Pat. Off. | A61B 17/39 |
| 0 558 297 A2 | 9/1993 | European Pat. Off. | A61M 25/00 |

(List continued on next page.)

OTHER PUBLICATIONS

Trimedyne, The Less Invasive Laser Advantage, Omni Spinal Introduction System.
PRNewswire ( Dec. 12, 1994), Two Physicians Perform First Outpatient Cervical Disc Procedure Using Laser Technology.
Introduction to the LDD Disc Kit, Oct. 16, 1996.
Mayer et al., Lasers in Percutaneous Disc Surgery: Beneficial Technology or Gimmick?, vol. 25 No. 251 (1993) pp. 38–44.

(List continued on next page.)

*Primary Examiner*—Lee Cohen
*Attorney, Agent, or Firm*—Wilson, Sonsini, Goodrich & Rosati

[57] ABSTRACT

Disclosed herein is a new arthroscopic probe with a concave distal tip which simultaneously constrains and cuts tissue. It is particularly adapted to cutting ligaments and tendons. Also disclosed is a thermal energy delivery apparatus which includes (a) a probe means with a distal end and a proximal end, wherein the distal end has a concave tip; (b) a first electrode means positioned at the distal end of the probe means, wherein the first electrode means is configured to deliver sufficient thermal energy to cut ligaments or tendons; and (c) a cabling means coupled to the proximal end of the probe means.

In another embodiment of the invention a controller for controlling the delivery of energy and liquid to a surgical instrument with a temperature sensor is disclosed. The energy is supplied by an energy source and the liquid is supplied by a pump. The controller includes a temperature and a flow regulator. The temperature regulator is coupled to the energy source and coupled to the pump. The temperature regulator is responsive to a first temperature indication from the temperature sensor to determine that the first temperature indication exceeds a setpoint and to reduce an energy level from the energy source. The flow regulator is coupled to the pump and coupled to the temperature regulator. The flow regulator includes responsiveness to the first temperature indication to increase a flow of the liquid from the pump.

4 Claims, 10 Drawing Sheets

U.S. PATENT DOCUMENTS

| | | | |
|---|---|---|---|
| 3,879,767 | 4/1975 | Substad | 3/1 |
| 3,886,600 | 6/1975 | Kahn et al. | 3/1 |
| 3,938,198 | 2/1976 | Kahn et al. | 3/1.912 |
| 3,945,375 | 3/1976 | Banko | 128/6 |
| 3,987,499 | 10/1976 | Scharbach et al. | 3/1.91 |
| 3,992,725 | 11/1976 | Homsy | 3/1 |
| 4,043,342 | 8/1977 | Morrison, Jr. | 128/303.14 |
| 4,074,718 | 2/1978 | Morrison, Jr. | 128/303.14 |
| 4,085,466 | 4/1978 | Goodfellow et al. | 3/1.91 |
| 4,129,470 | 12/1978 | Homsy | 156/155 |
| 4,134,406 | 1/1979 | Iglesias | 128/303.15 |
| 4,224,696 | 9/1980 | Murray et al. | 3/1.911 |
| 4,224,697 | 9/1980 | Murray et al. | 3/1.911 |
| 4,326,529 | 4/1982 | Doss et al. | 128/303.1 |
| 4,344,193 | 8/1982 | Kenny | 3/1.911 |
| 4,362,160 | 12/1982 | Hiltebrandt | 128/303.15 |
| 4,375,220 | 3/1983 | Matvias | 128/804 |
| 4,381,007 | 4/1983 | Doss | 128/303.1 |
| 4,397,314 | 8/1983 | Vaguine | 128/399 |
| 4,476,862 | 10/1984 | Pao | 128/303.17 |
| 4,483,338 | 11/1984 | Bloom et al. | 128/303.13 |
| 4,517,965 | 5/1985 | Ellison | 128/20 |
| 4,517,975 | 5/1985 | Garito et al. | 128/303.13 |
| 4,590,934 | 5/1986 | Malis et al. | 128/303.14 |
| 4,593,691 | 6/1986 | Lindstrom et al. | 128/303.14 |
| 4,597,379 | 7/1986 | Kihn et al. | 128/1 R |
| 4,601,705 | 7/1986 | McCoy | 604/94 |
| 4,651,734 | 3/1987 | Doss et al. | 128/303.14 |
| 4,811,733 | 3/1989 | Borsanyi et al. | 128/303.14 |
| 4,815,462 | 3/1989 | Clark | 128/305 |
| 4,838,859 | 6/1989 | Strassmann | 604/95 |
| 4,846,175 | 7/1989 | Frimberger | 128/303.15 |
| 4,873,976 | 10/1989 | Schreiber | 128/334 R |
| 4,894,063 | 1/1990 | Nashef | 623/13 |
| 4,895,148 | 1/1990 | Bays et al. | 606/213 |
| 4,907,585 | 3/1990 | Schachar | 606/28 |
| 4,907,589 | 3/1990 | Cosman | 606/34 |
| 4,924,865 | 5/1990 | Bays et al. | 606/77 |
| 4,924,882 | 5/1990 | Donovan | 606/45 |
| 4,944,727 | 7/1990 | McCoy | 604/95 |
| 4,950,234 | 8/1990 | Fujioka et al. | 604/60 |
| 4,955,882 | 9/1990 | Hakky | 606/14 |
| 4,966,597 | 10/1990 | Cosman | 606/50 |
| 4,976,709 | 12/1990 | Sand | 606/5 |
| 4,976,715 | 12/1990 | Bays et al. | 606/77 |
| 4,998,933 | 3/1991 | Eggers et al. | 606/41 |
| 5,007,908 | 4/1991 | Rydell | 606/47 |
| 5,009,656 | 4/1991 | Reimels | 606/48 |
| 5,085,657 | 2/1992 | Ben-Simhon | 606/42 |
| 5,085,659 | 2/1992 | Rydell | 606/47 |
| 5,098,430 | 3/1992 | Fleenor | 606/42 |
| 5,100,402 | 3/1992 | Fan | 606/41 |
| 5,103,804 | 4/1992 | Abele et al. | 128/4 |
| 5,114,402 | 5/1992 | McCoy | 604/95 |
| 5,152,748 | 10/1992 | Chastagner | 604/95 |
| 5,178,620 | 1/1993 | Eggers et al. | 606/41 |
| 5,186,181 | 2/1993 | Franconi et al. | 128/804 |
| 5,191,883 | 3/1993 | Lennox et al. | 128/401 |
| 5,192,267 | 3/1993 | Shapira et al. | 604/22 |
| 5,201,729 | 4/1993 | Hertzmann et al. | 606/2 |
| 5,201,730 | 4/1993 | Easley et al. | 606/4 |
| 5,201,731 | 4/1993 | Hakky | 606/15 |
| 5,213,097 | 5/1993 | Zeindler | 128/401 |
| 5,230,334 | 7/1993 | Klopotek | 128/399 |
| 5,242,439 | 9/1993 | Larsen et al. | 606/15 |
| 5,242,441 | 9/1993 | Avitall | 606/41 |
| 5,261,906 | 11/1993 | Pennino et al. | 606/46 |
| 5,267,994 | 12/1993 | Gentelia et al. | 606/15 |
| 5,275,151 | 1/1994 | Shockey et al. | 128/4 |
| 5,279,559 | 1/1994 | Barr | 604/95 |
| 5,284,479 | 2/1994 | de Jong | 604/60 |
| 5,304,169 | 4/1994 | Sand | 606/5 |
| 5,308,311 | 5/1994 | Eggers et al. | 606/28 |
| 5,311,858 | 5/1994 | Adair | 128/4 |
| 5,320,115 | 6/1994 | Kenna | 128/898 |
| 5,323,778 | 6/1994 | Kandarpa et al. | 128/653.2 |
| 5,334,193 | 8/1994 | Nardella | 606/41 |
| 5,342,357 | 8/1994 | Nardella | 606/40 |
| 5,348,554 | 9/1994 | Imran et al. | 606/41 |
| 5,352,868 | 10/1994 | Denen et al. | 219/501 |
| 5,354,331 | 10/1994 | Schachar | 623/4 |
| 5,364,395 | 11/1994 | West, Jr. . | |
| 5,366,443 | 11/1994 | Eggers et al. | 604/114 |
| 5,366,490 | 11/1994 | Edwards et al. | 607/99 |
| 5,382,247 | 1/1995 | Cimino et al. | 606/33 |
| 5,397,304 | 3/1995 | Truckai | 604/95 |
| 5,401,272 | 3/1995 | Perkins | 606/15 |
| 5,415,633 | 5/1995 | Lazarus et al. | 604/95 |
| 5,423,806 | 6/1995 | Dale et al. | 606/15 |
| 5,433,739 | 7/1995 | Sluijter et al. | 607/99 |
| 5,437,661 | 8/1995 | Rieser | 606/15 |
| 5,437,662 | 8/1995 | Nardella | 606/40 |
| 5,451,223 | 9/1995 | Ben-Simhon | 606/42 |
| 5,458,596 | 10/1995 | Lax et al. | 606/31 |
| 5,464,023 | 11/1995 | Viera | 128/772 |
| 5,465,737 | 11/1995 | Schachar | 128/898 |
| 5,484,403 | 1/1996 | Yoakum et al. | 604/59 |
| 5,484,432 | 1/1996 | Sand | 606/5 |
| 5,484,435 | 1/1996 | Fleenor et al. | 606/46 |
| 5,487,757 | 1/1996 | Truckai et al. | 607/122 |
| 5,498,258 | 3/1996 | Hakky et al. | 606/15 |
| 5,500,012 | 3/1996 | Brucker et al. | 607/122 |
| 5,507,812 | 4/1996 | Moore | 623/13 |
| 5,514,130 | 5/1996 | Baker | 606/41 |
| 5,524,338 | 6/1996 | Martyniuk et al. | 29/825 |
| 5,527,331 | 6/1996 | Kresch et al. | 606/170 |
| 5,542,920 | 8/1996 | Cherif Cheikh | 604/57 |
| 5,542,945 | 8/1996 | Fritzsch | 606/48 |
| 5,569,242 | 10/1996 | Lax et al. | 606/42 |
| 5,599,356 | 2/1997 | Edwards et al. | 607/122 |
| 5,630,839 | 5/1997 | Corbett, III et al. | 607/137 |
| 5,681,282 | 10/1997 | Eggers et al. | 604/114 |
| 5,683,366 | 11/1997 | Eggers et al. | 604/114 |
| 5,688,270 | 11/1997 | Yates et al. | 606/51 |
| 5,697,909 | 12/1997 | Eggers et al. | 604/114 |
| 5,718,702 | 2/1998 | Edwards | 606/41 |
| 5,782,795 | 7/1998 | Bays | 606/22 |
| 5,810,809 | 8/1998 | Rydell | 606/49 |

FOREIGN PATENT DOCUMENTS

| | | | |
|---|---|---|---|
| 0 566 450 A1 | 10/1993 | European Pat. Off. | A61N 5/02 |
| 0 572 131 A1 | 12/1993 | European Pat. Off. | A61B 17/39 |
| 0 682 910 A1 | 11/1995 | European Pat. Off. | A61B 1/00 |
| 0 479 482 B1 | 5/1996 | European Pat. Off. | A61B 17/39 |
| 0 729 730 A1 | 9/1996 | European Pat. Off. | A61B 17/32 |
| 0 737 487 A2 | 10/1996 | European Pat. Off. | A61M 25/01 |
| 0 783 903 A1 | 7/1997 | European Pat. Off. | A61N 5/04 |
| 1122634 | 9/1956 | France | A61F 19/00 |
| 2 645 008 | 3/1989 | France | A61B 17/32 |
| 2 645 008 | 10/1990 | France | A61B 17/32 |
| 3511107A1 | 10/1986 | Germany | A61B 17/39 |
| 3632197A1 | 3/1988 | Germany | A61B 10/00 |
| 39 18316 | 3/1990 | Germany | A61B 17/39 |
| 5-42166 | 5/1993 | Japan | A61B 17/39 |
| 637118 | 12/1978 | U.S.S.R. | A61B 17/18 |
| 1 340 451 | 12/1973 | United Kingdom | A61F 1/00 |
| 2160102 | 12/1985 | United Kingdom | 606/45 |
| 2 164 473 | 3/1990 | United Kingdom | A61B 17/36 |
| WO 82/02488 | 8/1982 | WIPO | A61B 17/39 |
| WO 85/02762 | 7/1985 | WIPO | A61B 17/36 |
| WO 92/05828 | 4/1992 | WIPO | A61M 25/00 |
| WO 92/10142 | 6/1992 | WIPO | A61B 17/36 |
| WO 93/01774 | 2/1993 | WIPO | A61F 7/12 |
| WO 93/16648 | 9/1993 | WIPO | A61B 17/32 |
| WO 93/20984 | 10/1993 | WIPO | B26D 1/11 |
| WO 95/01814 | 1/1995 | WIPO | A61N 5/02 |
| WO 95/10981 | 4/1995 | WIPO | A61B 8/12 |
| WO 95/13113 | 5/1995 | WIPO | A61N 5/02 |
| WO 95/18575 | 7/1995 | WIPO | A61B 17/39 |
| WO 95/20360 | 8/1995 | WIPO | A61B 17/39 |

| | | | |
|---|---|---|---|
| WO 95/25471 | 9/1995 | WIPO | A61B 17/39 |
| WO 95/30373 | 11/1995 | WIPO | A61B 17/00 |
| WO 95/30377 | 11/1995 | WIPO | A61B 17/39 |
| WO 95/34259 | 12/1995 | WIPO | A61F 5/48 |
| WO 96/11638 | 4/1996 | WIPO | A61B 17/32 |
| WO 96/32051 | 10/1996 | WIPO | A61B 1/00 |
| WO 96/32885 | 10/1996 | WIPO | A61B 5/04 |
| WO 96/34559 | 11/1996 | WIPO | A61B 5/0402 |
| WO 96/34568 | 11/1996 | WIPO | A61B 17/36 |
| WO 96/34571 | 11/1996 | WIPO | A61B 17/39 |
| WO 96/39914 | 12/1996 | WIPO | A61B 1/00 |
| WO 97/06855 | 2/1997 | WIPO | A61N 1/40 |
| WO 98/07468 | 2/1998 | WIPO | A61N 1/40 |
| WO 98/17190 | 4/1998 | WIPO | A61B 18/00 |

OTHER PUBLICATIONS

Schatz et al., Preliminary Experience With Percutaneous Laser Disc Decompression in the Treatment of Sciatica, vol. 38 No. 5, Oct. 1995, pp. 432–436.

Savitz M. A., Same–day Microsurgical Arthroscopic lateral–approach Laser–assisted (SMALL) Fluoroscopic Discectomy, vol. 80, Jun. 1994 pp. 1039–1045.

Bosacco et al., Functional Results of Percutaneous Laser Discectomy, Dec. 1996, pp. 825–828.

Sluijter M.E., The Use of Radiofrequency lesions For Pain Relief in Failed Back Patients, vol. 10 No. 1 (1988).

Cosman et al., Theoretical Aspects of Radiofrequency lesions in the Dorsal Root Entry Zone, vol. 15 No. 6 (1984) pp. 945–950.

Wilkins et al., Neurosurgery: Method of Making Nervous System Lesions, ch. 337, pp. 2490–2499.

Yonezawa et al., The System and Procedure of percutaneous Intradiscal Laser Nucleotomy, vol. 15 No. 5 (1990) pp. 1175–1185.

Kolarik et al., Photonucleolysis of Intervertebral Disc and it's Herniation, (1990).

Gottlob et al.,Lasers in Surgery and Medicine: Holmium:YAG Laser Ablation of Human Intervertebral Disc: Preliminary Evaluation, vol. 12, (1991) pp. 86–91.

Buchelt et al., Lasers in Surgery and Medicine: Fluorescence Guided Excimer Laser Ablation of Intervertebral Discs In Vitro, vol. 11, (1991) pp. 280–286.

Choy et al., Percutaneous Laser Disc Decompression: A New Therapeutic Modality, vol. 17 No. 8, (1992) pp. 949–956.

Sluijter et al., Persistant Pain, Modern Methods of Treatment: Treatment of Chronic Back and neck Pain, vol. 3, (1981) pp. 141–179.

Sluijter, Int Disabil Studies: The use of Radio Frequency Lesions For Pain Relief in Failed Back, vol. 10, Sep. 4, 1996, pp. 37–43.

Shatz et al., CJS JCC Preliminary Experience With Percutaneous Laser Disc Decompression in the Treatment of Sciatica, vol. 38 No. 5, Oct. 1995 pp. 432–436.

Gerber et al., DER Orthopade: Offene Laserchirurgie am Bewegungsapparat, vol. 25, (1996) pp. 56–63.

Gehring W. J., Exploring the Homeobox, (1993), pp. 215–221.

Kelly L.E., Purification and Properties of a 23kDa Ca2+ –binding Protein, (1990) 271, pp. 661–666.

Sluyter, Radiofrequency Lesions in the Treatment of Cervical Pain Syndromes, Radionics, Inc. (1989).

Buchelt et al., Lasers in Surgery and Medicine:Erb:YAG and Hol:YAG Laser Ablation of Meniscus and Intervertebral Discs, vol. 12 No. 4, (1992) pp. 375–381.

Leu et al., Der Orthopade: Endoskopie der Wirbelsaule: Minimal–invasive Therapie, vol. 21, (1992) pp. 267–272.

Phillips et al., JMRI: MR Imaging of Ho: YAG Laser Diskectomy with Histologic Correlation, vol. 3 No. 3, May/Jun. 1993.

Bromm et al., Human Neurobiology: Nerve Fibre Discharges, Cerebral Potentials and Sensations Induced by CO2 laser Stimulation, vol. 3, (1984) pp. 33–40.

Kolarik et al., Photonucleolysis of Intervertebral Disc and it's Herniation, vol. 51, (1990) pp. 69–71.

Vorwerck et al., Laserablation des Nucleus Pulposus: Optische Eigenschaften von Degeneriertem Bandscheibengewebe im Wellenlangenbereich von 200 bis 2200nm, vol. 151 No. 6, (1989) pp. 725–728.

Wolgin et al., Excimer Ablation of Human Intervertebral Disc at 308 Nanometers, vol. 9, (1989) pp. 124–131.

Davis, Early experience with Laser Disc Decompression, vol. 79 No. 1, (1992) j. Florida M.A.

Quigley et al., Laser Discectomy: Comparison of Systems, vol. 19 No. 3 (1994) pp. 319–322.

Mehta et al., The Treatment of Chronic back Pain: A Preliminary survey of the Effect of Radiofrequency Denervation of the Posterior Vertebral Joints, vol. 34 (1979) pp. 768–775.

Patil et al., Percutaneous Discectomy Using the Electomagnetc Field Focusing Probe: A Feasability Study.

McCulloch et al., CMA Journal: Percutaneous Radiofrequency Lumbar Rhizolysis (rhizotomy), vol. 116, Jan. 8, 1977.

Yonezawa et al., The System and Procedure of Percutaneous Intradiscal Laser Nucleotomy, vol. 15 No. 11 (1990).

Sminia et al., Effects of 434 MHz Microwave Hyperthermia applied to the rat in the region of the cervical Spinal Cord, vol. 3 No. 5 (1987) pp. 441–452.

Sluijter et al., Treatment of Chronic Back and Neck Pain by Percutaneous Therman Lesions, vol. 3 (1981.

Auhll, Richard A., "The Use of the Resectoscope in Gynecology." Biomedical Business International, Oct. 11, 1990, pp. 91–93.

Christian, C. et al., "Allograft Anterior Cruciate Ligament Reconstruction with Patellar Tendon: An Endoscopic Technique", Operative Techniques in Sports Medicine, vol. 1, No. 1, Jan. 1993, pp. 50–57.

Houpt, J. et al., "Experimental Study of Temperature Distributions and Thermal Transport During Radiofrequency Current Therapy of the Intervertebral Disc", Spine, vol. 21, No. 15, (1996), pp. 1808–1813.

Troussier, B. et al., "Percutaneous Intradiscal Radio–Frequency Thermocoagulation: A Cadaveric Study", Spine, vol. 20, No. 15, (Aug. 1995), pp. 1713–1718.

Beadling, L., "Bi–Polar electrosurgical devices: Sculpting the future of arthroscopy", Orthopedics today, vol. 17, No. 1, Jan. 1997, 4 pages.

Ellman International Mfg., Inc., 1989, Catalog, pp. 1–15, 20.

Cosset, J.M., Resistive Radiofrequency (Low Freqency) Interstitial Heating (RF Technique), Interstitial Hyperthermia, Dec. 6, 1993, pp. 3–5, 37.

Attachment I: Competitive Literature on Generators with Bipolar Capabilities, IME Co., Ltd., pp. 60–86.

Attachment II: Competitive Literature on Bipolar Forceps and Footswitch Controls, IME Co., Ltd. pp. 87–104.

Glenohumeral Joint
Lateral (side) View

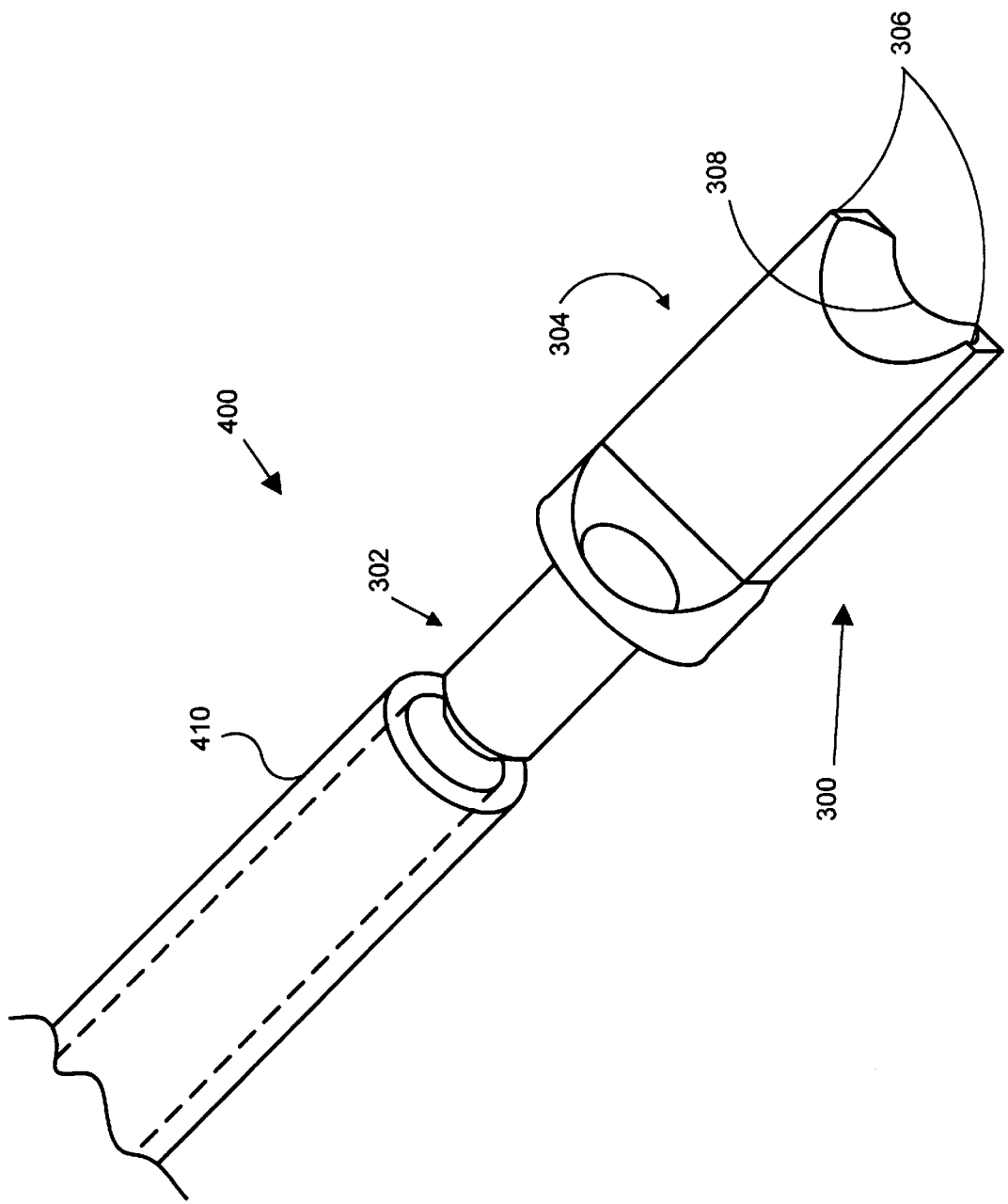

CONCAVE PROBE FOR ARTHROSCOPIC SURGERY

This application claims priority to Provisional Application Ser. No. 60/037,782, filed Feb. 12, 1997, which is incorporated herein by reference in its entirety.

BACKGROUND OF THE INVENTION

1. FIELD OF USE

The present invention is in the field of medical devices which deliver radio-frequency energy to cut tissue. More specifically, the invention is in the field of cutting probes for arthroscopic surgery.

2. BACKGROUND

Arthroscopic surgery is becoming increasingly popular, because it generally does less damage than open procedures, produces less scarring in and around joints, and results in faster healing and return of the patient to full productivity.

Nevertheless, arthroscopic surgery has its limitations. The surgeon must operate through a narrow tube, which is awkward. Only one probe can be used at a time. Often the viewing camera is positioned at an angle different from the surgeon's normal gaze. This contrasts with "open surgery" where the surgeon has relative ease of viewing the surgical site and can freely move both hands, even utilizing the hands of colleagues.

In view of such difficulties of arthroscopic surgery, it is understandable that laser, microwave and radio-frequency (RF) probes which simultaneously cut and coagulate are preferred. However, current probes are poorly adapted to certain activities, such as cutting narrow tendons or ligaments. Current probes have convex, pointed and/or flat tips. U.S. Pat. No. 5,308,311, issued May 3, 1994 to Eggers and Shaw, is exemplary in that it discloses a laser probe with a pointed tip and convex side. With current probes, the surgeon has little control when pressing against a tough ligament. Now as the surgeon cuts through one portion of the ligament, the probe slips out of position. The surgeon must reapproximate the probe and cut again, an inefficient process. And, unless the surgeon is able to stop pressure at exactly the right time, the probe may slip and cut an adjacent structure. Because the surgeon must repeatedly reapproximate and cut the ligament, the surgeon has difficulty in cleanly ablating the ligament or tendon. Thus, there are certain procedures that surgeons still prefer to perform in the "open." Unfortunately, this often results in bigger scars, longer convalescence, and more irritation of an already irritated joint.

What is needed is a probe that can simultaneously direct the tendon to the energy source (e.g., RF) and apply RF to cleanly and smoothly ablate the tendon or ligament. The advantage is that some procedures that have been considered too awkward or difficult to perform by arthroscopy can now be performed more effectively by arthroscopy.

SUMMARY OF THE INVENTION

A thermal energy delivery apparatus is disclosed which has a probe means including a distal end and a proximal end, wherein the distal end has a concave tip. A first electrode means is also positioned at the distal end of the probe means, so that the first electrode means is configured to deliver sufficient thermal energy to cut ligaments or tendons. The thermal energy delivery apparatus also includes a cabling means coupled to the proximal end of the probe means. The cabling means can be either permanently or impermanently coupled to the probe means.

In another embodiment, there is an RF probe comprising a distal tip, wherein the distal tip has a concave curve and an electrode, whereby the concave curve on the distal tip helps constrain tissue for cutting. In another embodiment, the RF probe has a concave curve with a sharp edge. In yet another embodiment, the RF probe has a concave curve separated from the lateral edges of the RF probe.

Another embodiment of this invention is a method of cutting a ligament or tendon by (a) providing an RF probe with a distal tip with a concave curve; (b) approximating the RF probe to the ligament or tendon to be cut; and (c) applying RF energy through the curve, thereby cutting the ligament, tendon, or other tissue.

In another embodiment of the invention a controller for controlling the delivery of energy and liquid to a surgical instrument with a temperature sensor is disclosed. The energy is supplied by an energy source and the liquid is supplied by a pump. The controller includes a temperature and a flow regulator. The temperature regulator is coupled to the energy source and coupled to the pump. The temperature regulator is responsive to a first temperature indication from the temperature sensor to determine that the first temperature indication exceeds a setpoint and to reduce an energy level from the energy source. The flow regulator is coupled to the pump and coupled to the temperature regulator. The flow regulator includes responsiveness to the first temperature indication to increase a flow of the liquid from the pump.

BRIEF DESCRIPTION OF THE DRAWINGS

FIGS. 4–11 show different monopolar and bipolar arrangements of the electrodes on the concave cutting tip.

DESCRIPTION OF SPECIFIC EMBODIMENTS

Figure 1:
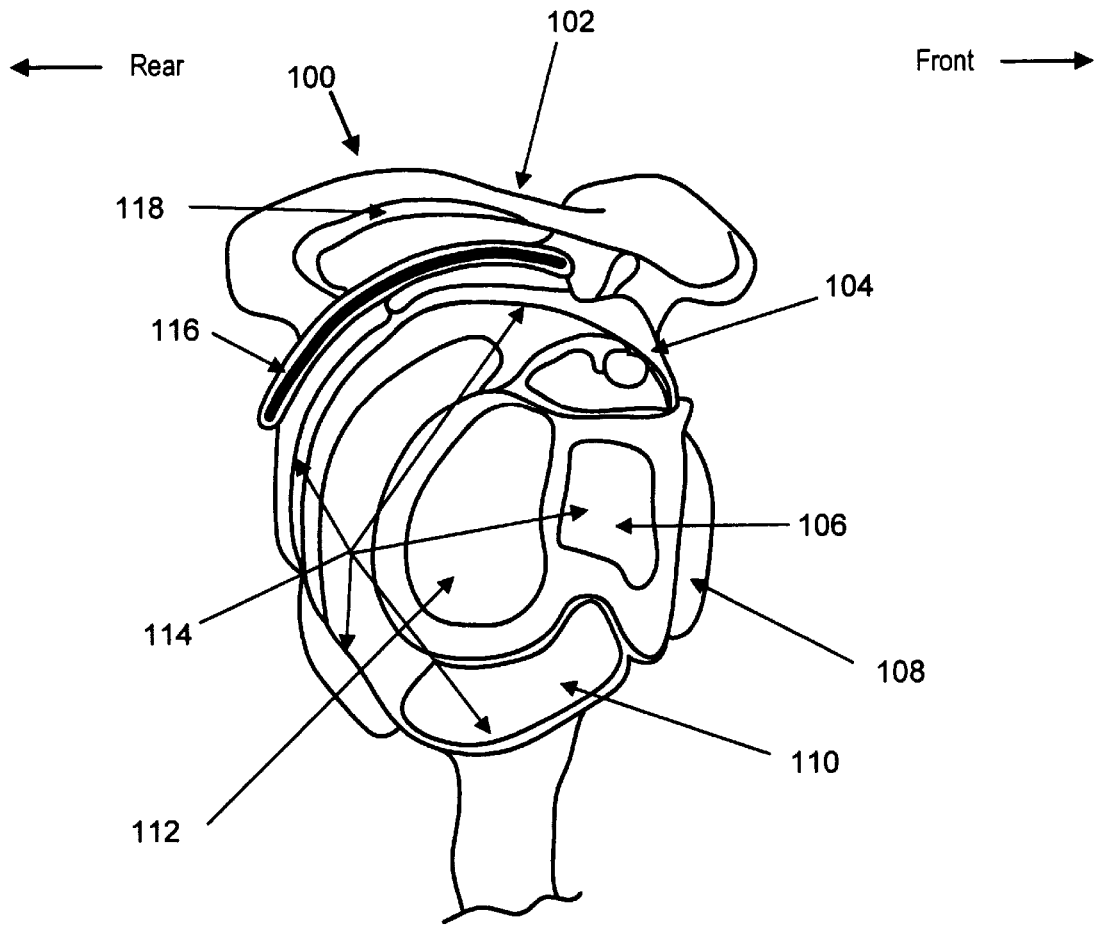
FIG. 1 is a lateral view of the internal structures of the glenohumeral joint.

The present invention arose out of an observation that, during an arthroscopy procedure, the surgeon could not access and cut cleanly the coracoacromial (CA) ligament shown in FIG. 1. This procedure is done in conjunction with a subacromial decompression, which makes a painful shoulder easier to move. If the cutting probe slips, the joint capsule could be damaged and even punctured, which would exacerbate an already painful joint. Thus, a concave rounded tip was designed which would center and position ligaments and could even be used to lift the ligament away from adjacent structures and avoid harm thereto.

This new style of tip has the advantage of being able to mechanically "gather" or constrain ligaments, tendons and other tissue into its center. This reduces the natural tendency of current cutting probes to slide off ligaments and tendons. This helps save time in that the surgeon is not repeatedly trying to center or approximate the probe tip on the target tissue.

FIG. 1 shows a lateral (side) view of a glenhumeral joint 100 and in particular the Coracoacromial ligament 102, the Superior glenohumeral ligament 104, the middle glenohumeral ligament 106, the Subscapularis Tendon 108 (joined to capsule), the Inferior Glenoheumeral ligament 110, the Glenoid "cup" with cartilage 112, the Joint Capsule 114, and the Bursa 116. The Joint Capsule 114 is comprised of 3GH ligaments and surrounding capsule. The Bursa 116 lubricates and acts like a shock absorber, and is usually removed when an SA decompression is performed. The area 118 is the area at which impingement usually occurs.

Figure 2:
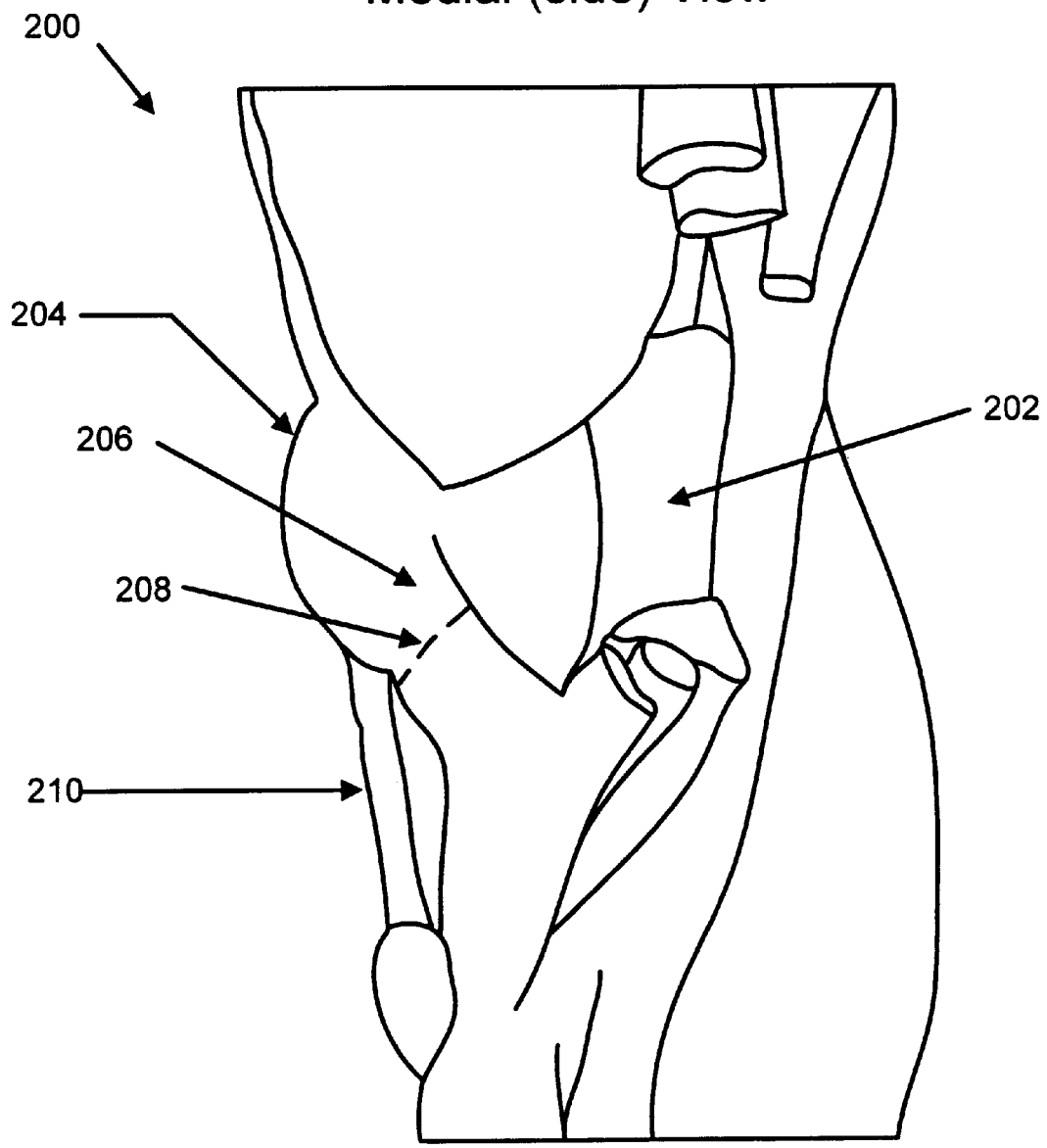
FIG. 2 is a medial side view of the knee joint.

FIG. 2 shows a medial (side) view of a glenhumeral joint 200, and in particular the Medial Collateral Ligament 202, the patella 204, the Medial Lateral Retinaculum 206, an incision line 208 for lateral release and the Patellar Ligament 210.

While CA surgery was the inspiration for this invention, use of this concave probe is not limited to a particular ligament or tendon, or even to those tissues. The concave cutting probe is adapted to cut all types of tendons and ligaments more effectively than blunt or rounded tip probes. As another example whose anatomy is shown in FIG. 2, the lateral retinaculum sometimes must be severed in some types of patellar dislocation or malignment, when the patella is not properly tracking in the trochlear notch. Severing the lateral retinaculum is called lateral retinacular release. With this concave-tip probe, the surgeon is able to position the ligament and sever it cleanly.

Figure 3:
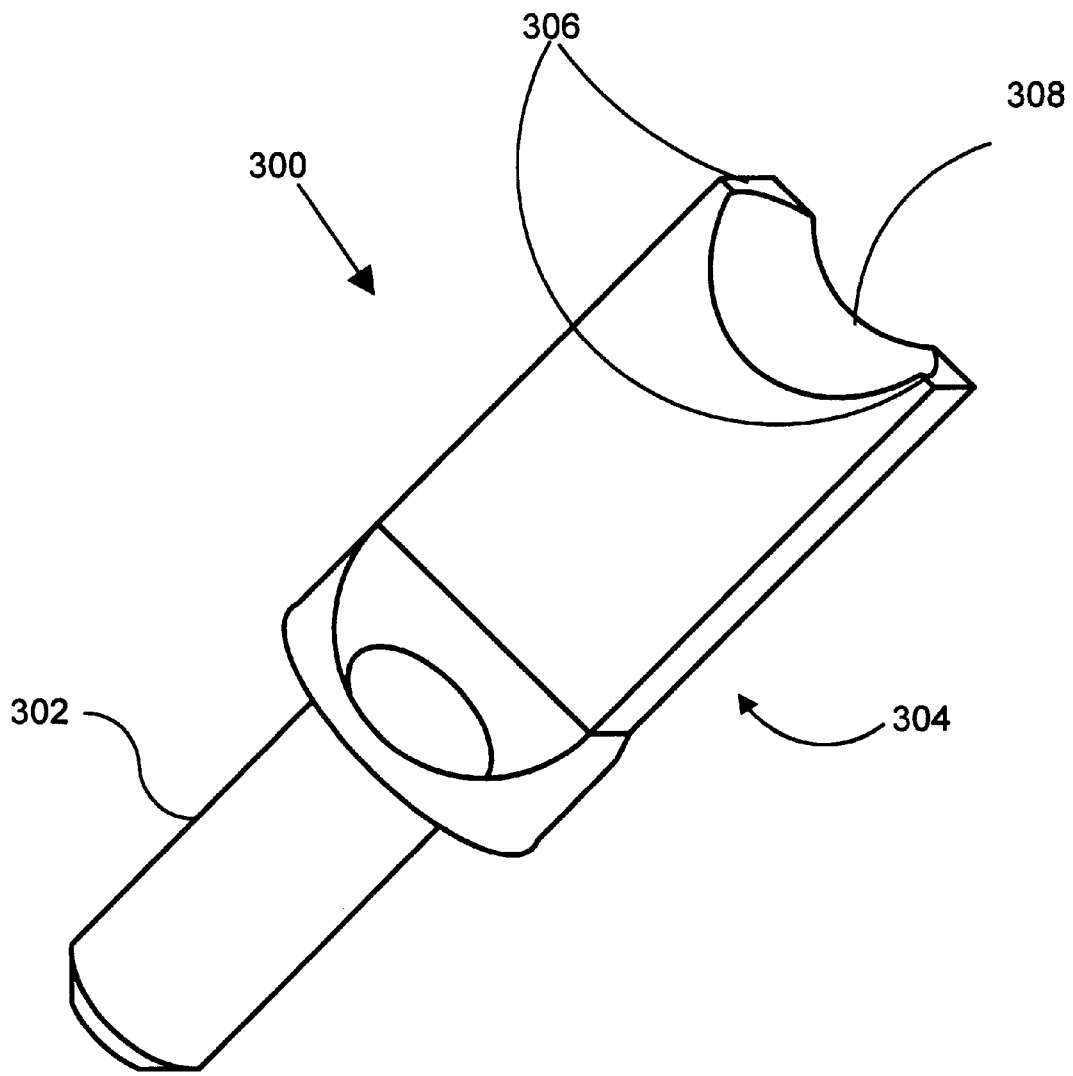
FIG. 3 is a perspective view of the concave cutting tip of the RF probe.

Turning now to the probe itself, FIG. 3 shows a concave edge 308 on a distal tip 304 of an RF probe head 300. This concave edge is designed to constrain tissue, tendons and ligaments. The concave curve has lateral edges 306 which are rounded, so that the probe does not "snag" on unwanted tissue as the surgeon maneuvers the probe into position. The cylindrical portion 302 of the distal tip 304 fits inside probe sheath 410, as shown in FIG. 4. The distal tip may have a variety of configurations, as shown in FIGS. 3–10. FIG. 4 shows probe 400 having a concave edge with less prominently rounded lateral edges. FIGS. 4–6 show a distal tip which is angled with respect to the sheath 410. This embodiment offers the advantage of helping the surgeon get around corners.

Figure 5A:
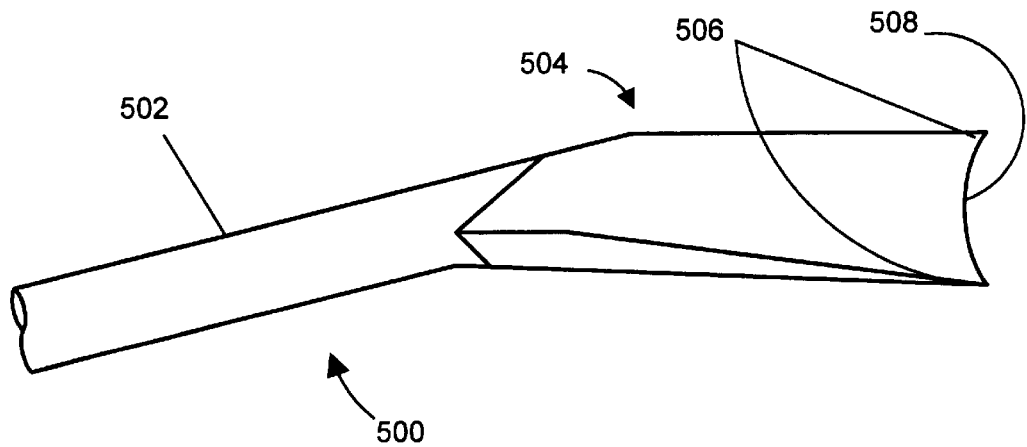
Figure 5B:
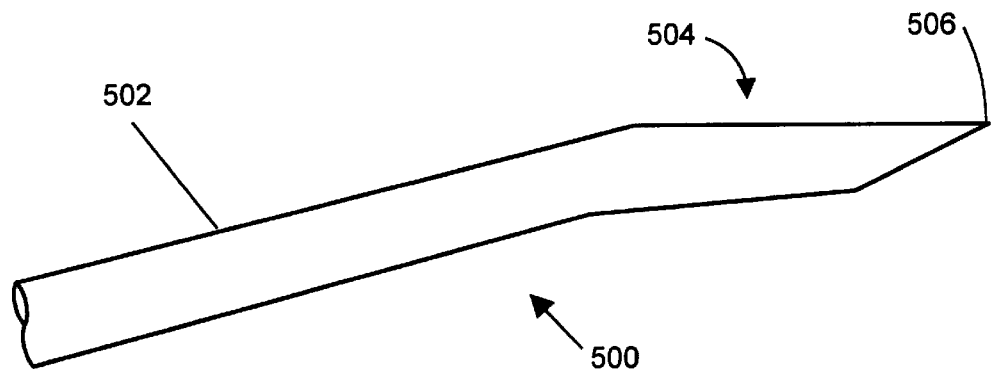
Figure 6:
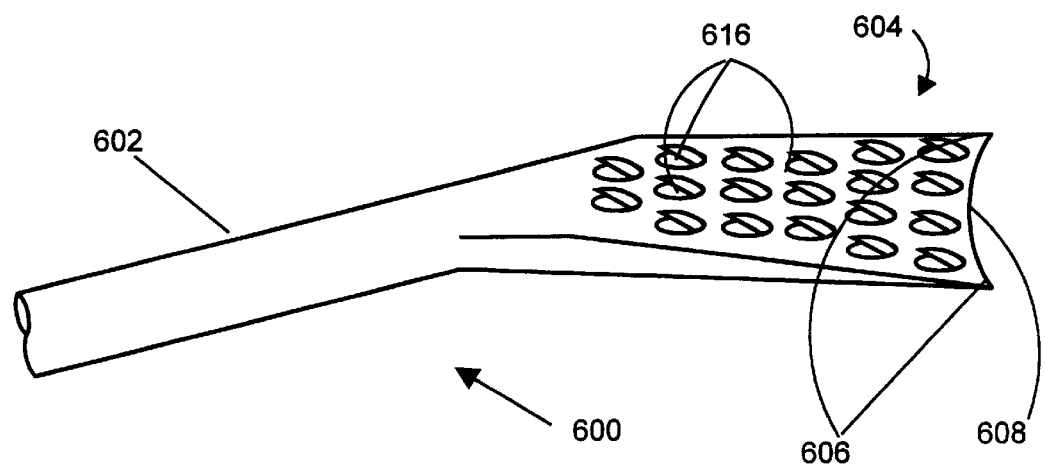

FIG. 5A shows an angled probe 500 consisting of a cylindrical portion 502 with a distal tip 504 having a concave edge 508 and lateral edges 506. FIG. 5B shows a side view of angled probe 500.

FIG. 6 shows an angled probe 600 with a specialized surface (not heated) which imparts a third function to the probe, namely scraping tissue. Probe 600 is comprised of a cylindrical portion 602, and a distal tip 604 which has a concave edge 608 and lateral edges 606. The surface of the flat portion of distal tip 604 contains rasps 616 which can be used for scraping tissue.

For cutting tissue, the distal tip has a first electrode and a second electrode located on lateral edges 606. The first and second electrodes can be operated in bipolar or monopolar mode. Bipolar is preferred and examples of "Taser" type electrodes are shown in FIGS. 7 and 8.

Figures 7, 8:
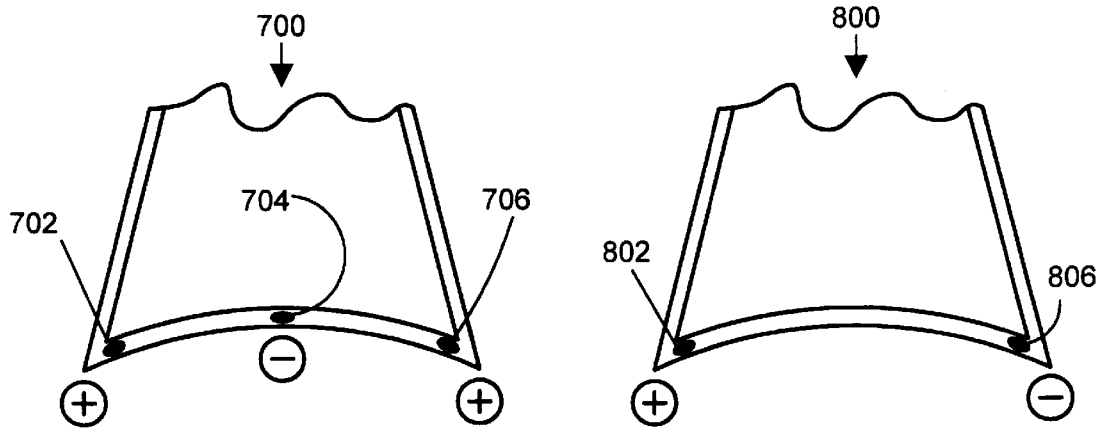
Figures 9, 10:
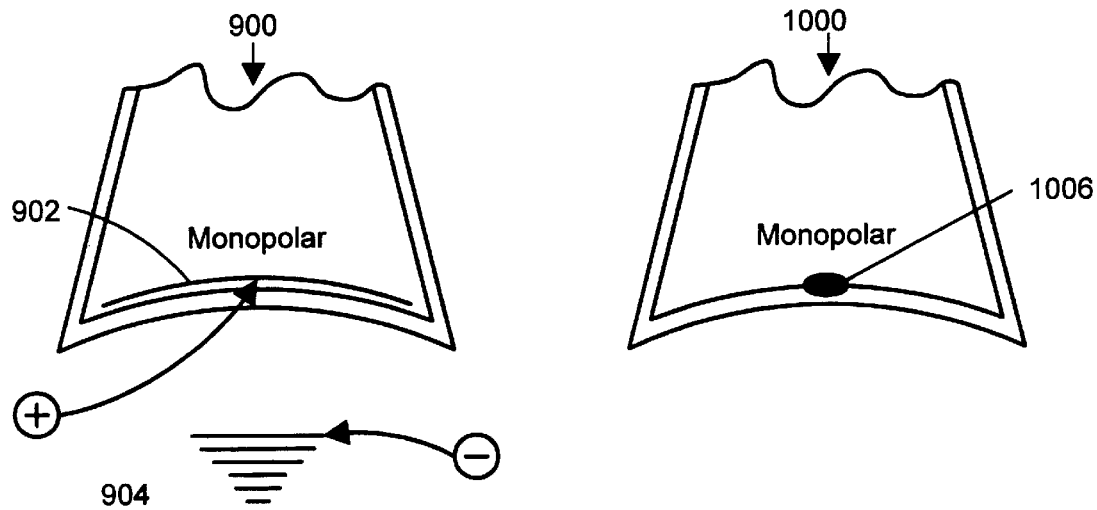
Figure 11:
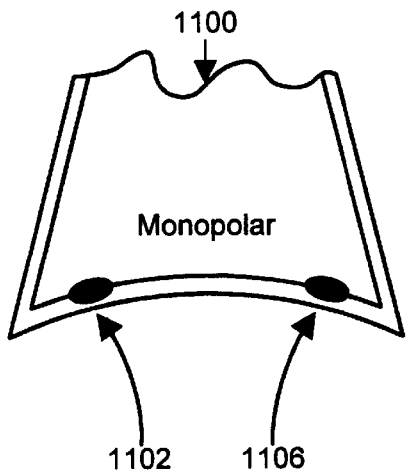

FIG. 7 shows a distal tip 700 having a three-pole, bipolar arrangement where, in addition to two side positive electrodes 702 and 706, there is a central negative electrode 704. FIG. 8 shows a distal tip 800 wherein two electrodes 802 and 806 are positioned in two small sites on the lateral edges of the concave curve. In this particular embodiment, electrode 802 is positive and electrode 806 is negative FIGS. 9–11 show exemplary monopolar arrangements. In FIG. 9, a single monopolar positive electrode 902 occupies a wide portion of the concave curve of distal tip 900. A return path 904 is provided and is attached to the patient's body to complete the circuit. In FIG. 10, there is one small active electrode 1006 located centrally on distal tip 1000. In FIG. 11 there are two active electrodes 1102 and 1106 in lateral positions on distal tip 1100. Suffice it to say that quite a variation in electrode design is contemplated for this concave curve.

To maintain the appropriate temperature for cutting tissue, the distal tip of the probe may also be equipped with a thermocouple, but such a thermocouple is optional in the concave-tipped probe.

Figure 12B:
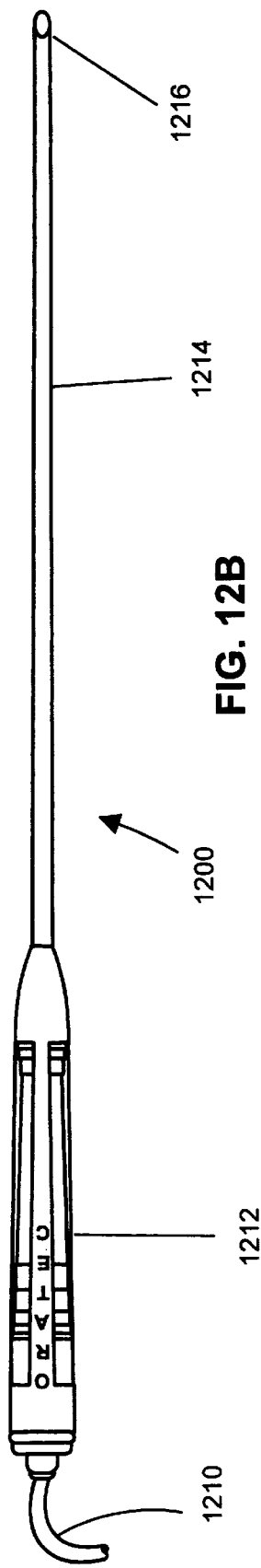
FIG. 12 shows an overview of an RF probe.
Figure 12A:
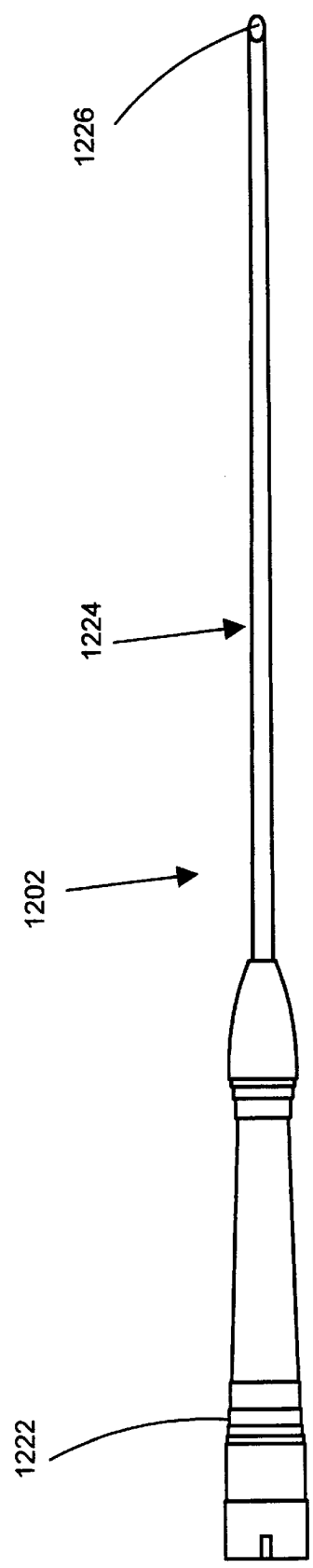
Figure 13:
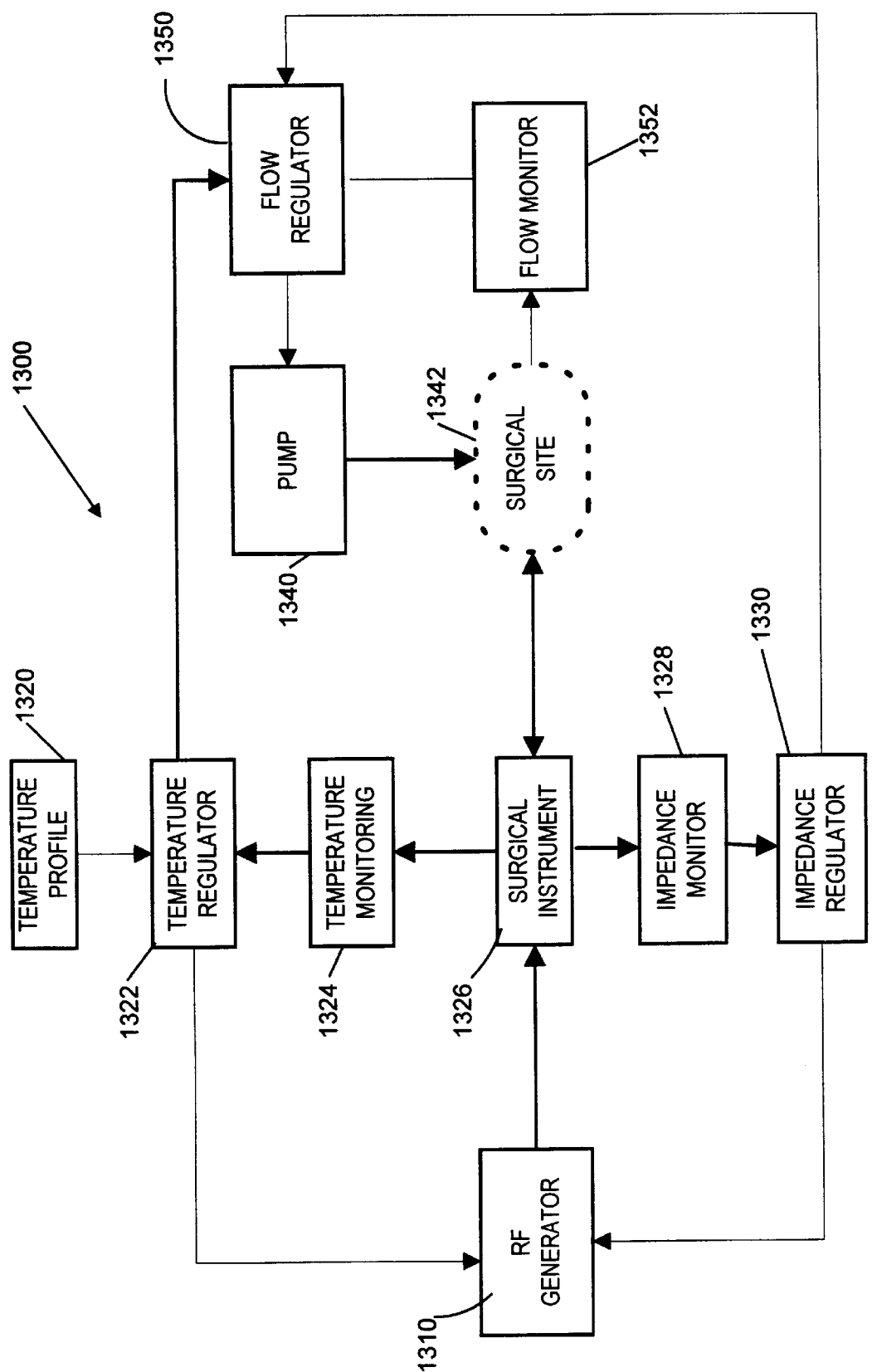
FIG. 13 is a block diagram illustrating a feedback system useful to control the temperature of electrodes of the present invention.

FIG. 12 illustrates the RF probe of a larger RF apparatus shown schematically in FIG. 13, which is a block diagram of a temperature/impedance feedback system useful with apparatus 1200.

FIG. 12A is an illustration of a cannula utilized in one embodiment of the invention. Cannula 1202 consists of a guide 1224 with an opening 1226 at its distal end. Cannula 1202 is attached at its proximal end to introducer 1222. As illustrated in FIG. 12B, surgical instrument 1200 consists of a handle 1212 to which is attached a power cord 1210, a probe 1214 and a probe tip 1216. Cannula 1202 is inserted into the surgical site on the patient. Surgical instrument 1200 is then inserted into cannula 1202 so that the tip 1216 protrudes from the opening 1226 in cannula 1202.

FIG. 13 is an electrical block diagram of an embodiment of the current invention in which both RF power and saline solution are applied to a surgical site, under unified control of controller 1300. The The RF power is applied to the site for cutting, cauterizing, ablating and sculpting of tissue. The saline solution is applied to the site for irrigation and in order to create a cavity in the area in which surgery is to be performed. In this embodiment it is advantageous to regulate RF delivery through both temperature and impedance monitoring. It is advantageous to monitor saline solution flow to maintain clarity at the site. There is also the opportunity for synergy between RF and saline delivery to the surgical site to provide, for example, a greater level of control of temperatures at the site.

The controller 1300 shown in FIG. 13 includes RF generator 1310, temperature profile 1320, temperature regulator 1322, temperature monitor 1324, surgical instrument 1326, impedance monitor 1328, impedance regulator 1330, pump 1340, flow regulator 1350 and flow monitor 1352.

The RF generator is capable of delivering monopolar or bipolar power to surgical instrument 1326. The surgical instrument contains a probe and tip which are positioned at the surgical site 1342. The impedance monitor 1328 obtains impedance measurements by, for example, measuring current and voltage and performing a RMS calculation. The measurements of the impedance monitor are delivered to impedance regulator 1330. The impedance regulator performs several functions. Generally the impedance regulator keeps the impedance levels within acceptable limits by controlling the power supplied by the RF generator 1310. In an embodiment of the current invention the impedance regulator can control the flow regulator 1350 to deliver more or less saline solution to the surgical site.

The temperature monitor 1324 can include one or more types of temperature sensors, e.g. thermocouples, thermistors, resistive temperature device (RTD), infrared detectors, etc. . The temperature sensor is positioned at the tip of the surgical instrument to provide temperature monitoring of the tip. The output of the temperature monitor is delivered to the temperature regulator 1322. The temperature regulator 1322 also accepts input from a temperature profile table 1320. The temperature profiles contained in this table may include time and temperature points which need to be achieved during surgery. The temperature regulator may control both the RF generator 1310 and the flow regulator 1350. When, for example, temperatures have increased beyond an acceptable limit, power supplied by the RF generator to the surgical instrument may be reduced. Alternately, the temperature regulator may cause the flow regulator 1350 to increase saline solution flow, thereby decreasing temperature at the surgical site. Conversely, the temperature regulator can interface with either the RF generator or the flow regulator when measured temperatures do not match the required temperatures called for in the temperature profile 1320. When this condition occurs, the temperature regulator can cause the RF generator to increase power supply to the surgical instrument. Alternately, the temperature regulator can cause the flow regulator to decrease saline solution flow to the surgical site, thereby allowing a fixed amount of RF energy to cause an increase in temperature at the surgical site. In another embodiment of the invention a flow monitor 1352 can be positioned at the surgical site. The flow monitor can monitor the volume of saline solution flow, the actual dimension of the cavity, the pressure created by the saline solution within the cavity or the optical clarity of the saline solution within the cavity. Any one of these and other monitored parameters can be utilized independently to regulate the flow of saline solution to the site by providing these measurements to the flow regulator. The flow regulator may be programmed to accommodate regulatory signals from both the temperature and impedance regulators, as well as the flow monitor and can be programmed to perform in whatever manner is desired by the user. The flow regulator interfaces with the pump 1340 to control the volume of saline solution delivered to the surgical site 1342.

An exemplary interaction of these various components is shown by way of the following example. Initially the temperature regulator and/or impedance regulator and the flow regulator deliver pre-programmed amounts of power and saline solution to the surgical site 1342. Each system operates independently. The flow regulator, for example, operates the pump to maintain saline solution flow within the desired parameters, i.e. clarity, pressure, flow rate, etc. The temperature regulator delivers pre-programmed time-based temperature profile to the surgical instrument 1326 from the RF generator 1310. When impedance levels fall below a lower threshold indicating that the instrument has been removed from the site, the RF generator is caused to terminate power supply to the surgical instrument. Alternately, when impedance levels exceed an upper threshold indicating that tissue is accumulating on the tip of the surgical instrument, thereby increasing resistance to current flow, pulses of RF power are delivered to the surgical instrument to cause the tissue to ablate from the tip, thereby decreasing the impedance of the tip. Alternately, the impedance regulator can at the upper threshold of impedance signal the surgeon audibly, visibly or in any other manner that the instrument itself needs to be cleaned before proceeding further with the surgery. If during the operation the flow regulator receives from either the temperature or impedance regulator a signal indicating that temperatures and/or impedance are exceeding acceptable levels, then flow can be increased to reduce temperature and/or clean the tip. Alternately, if the flow regulator receives signals indicating that temperature and/or impedance are too low, then the flow regulator can reduce saline solution flow to allow greater heating at the surgical site 1342. When the control signals from the temperature regulator 1322 and/or the impedance regulator 1330 cease, the flow regulator 1350 returns to normal operation.

Figure 14:
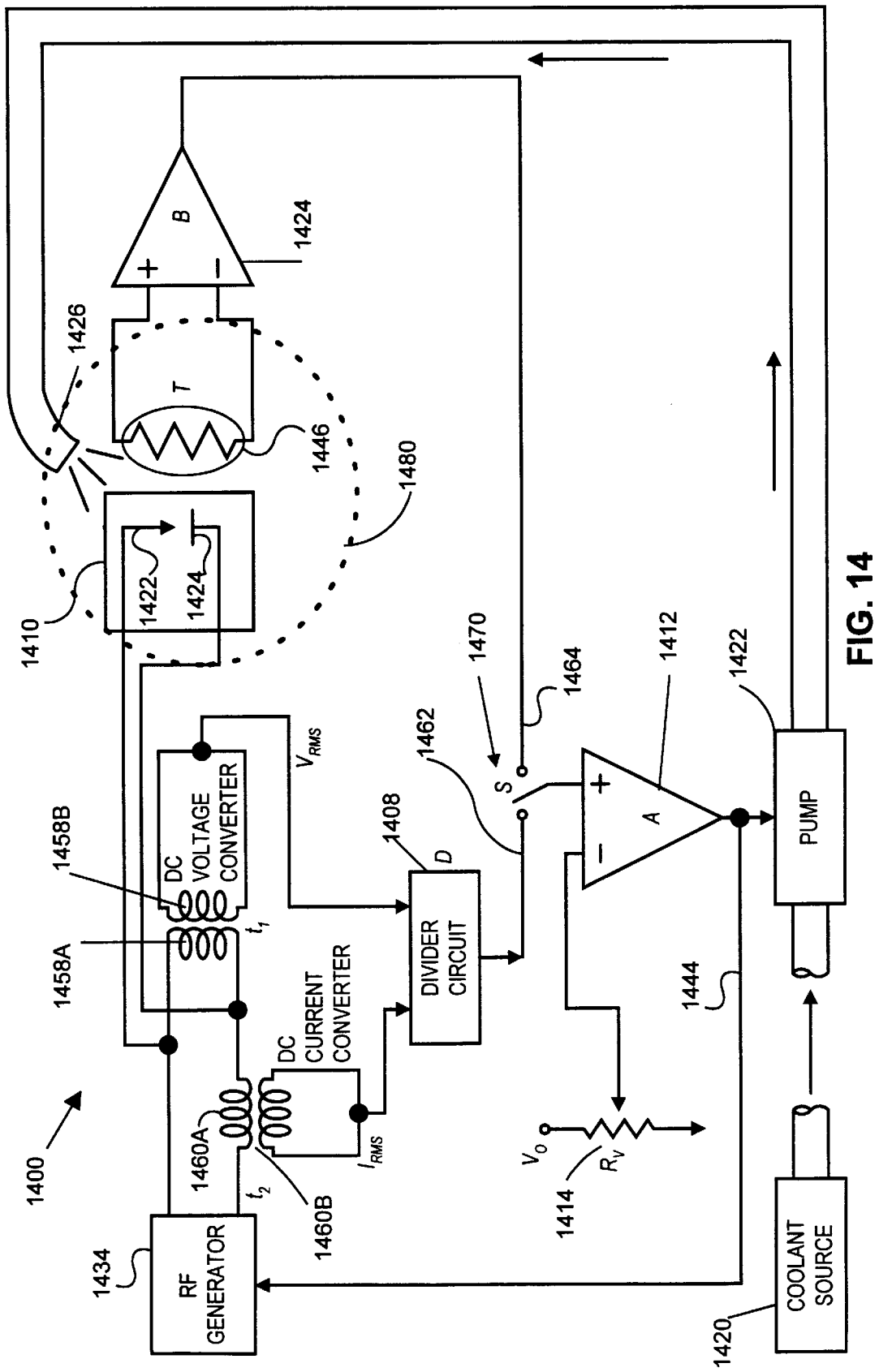
FIG. 14 illustrates a circuit useful to implement the feedback system of FIG. 13.

FIG. 14 shows an alternate embodiment of the invention to that discussed above in connection with FIG. 13. In this embodiment fluid flow and RF generation are regulated either by temperature regulator or impedance. There is no independent flow monitor such as the one shown and discussed above in connection with the embodiment in FIG. 13. RF generator 1434 is coupled to first and second electrodes 1422 and 1424 to apply a biologically safe voltage to surgical site 1480. In the embodiment shown in FIG. 14 the surgical instrument 1410 is represented as a bipolar ablation device. The circuitry shown herein is equally applicable to monopolar surgical instruments as well. First and second electrodes 1422 and 1424 of the bipolar device are connected to a primary side of transformer windings 1458A and 1460A. The common primary windings 1458A and 1460A are magnetically coupled with a transformer core to secondary windings 1458B and 1460B. The transformer windings 1458A–B are part of transformer t1. The transformer windings 1460A–B are part of transformer t2. The primary windings of the first transformer t1 couple the output voltage of surgical instrument 1410 to the secondary windings 1458B. The primary windings 1460A of the second transformer t2 couple the output current of surgical instrument 1410 to the secondary windings 1460B. Measuring circuits connected to the secondary windings 1458B and 1460B determine the root mean square (RMS) values or magnitudes of the current end voltage. These values, represented as voltages, are inputted to dividing circuit 1408 to mathematically calculate, by dividing the RMS voltage value by the RMS current value the impedance of the surgical site 1480.

The output voltage 1462 of the divider circuit 1408 is coupled to a pole of single pole double throw (SPDT) switch 1470. The other pole 1464 of the switch is connected to the output of thermal coupler amplifier 1424. The inputs of thermal couple amplifier 1424 are connected to the temperature sensor 1446 which measures temperatures at the surgical site 1480. Switch 1470 serves therefore to couple either the impedance circuitry or the temperature monitoring circuitry to the positive (+) input of comparator 1412. Voltage reference 1414 supplies a voltage across a variable resistor Rv, thus allowing one to manually adjust the voltage presented to the negative input of comparator 1412. This voltage represents a maximum impedance value beyond which power will not be applied to electrode 1422. In an embodiment in which the switch 1470 is connected to the divider circuit 1408, impedance values greater than the maximum cutoff impedance determined by resistor 1414 result in comparator 1412 reducing the power supplied by RF generator 1434 to the surgical site. Alternately, the comparator can deliver a signal to pump 1422 causing it to increase the fluid flow from coolant source 1420 through nozzle 1426 positioned at the surgical site 1480. This will reduce temperatures at the site. Alternately, when switch 1470 connects pole 1464 to the positive input of comparator 1412 temperature rather than impedance can be utilized to control either the RF generator 1434 or the pump 1422. Comparator 1412 can be of any commercially available type that is able to control the amplitude and pulse width modulation of RF generator 1434. The temperature as discussed above within the surgical site 1480 can be controlled based on tissue impedance when switch 1470 connects pole 1462 to the comparator 1412. Alternately, control can be based on tissue temperature as represented when the switch 1470 connects pole 1464 to the comparator 1412. In an embodiment switch 1470 is activated to allow impedance node 1462 to enter the positive (+) input terminal of comparator 1412. This signal along with the reference voltage applied to the negative (−) input terminal actuates comparator 1412 to produce an output signal. If the selected tissue ablation site is heated to a biologically damaging temperature, the tissue impedance will exceed a selected impedance value seen at the negative (−) input terminal, thereby reducing power to the RF generator 1434 and/or increasing flow from pump 1422. The output signal of comparator 1412 may be utilized to sound an alarm or give a visual indication of an over temperature condition or, as discussed above, to reduce power and/or disable the RF generator.

Energy source 1434 is shown as providing RF energy, but is not limited to RF and can include microwave, ultrasonic, coherent and incoherent light thermal transfer and resistance heating.

Figures 15A, 15B:
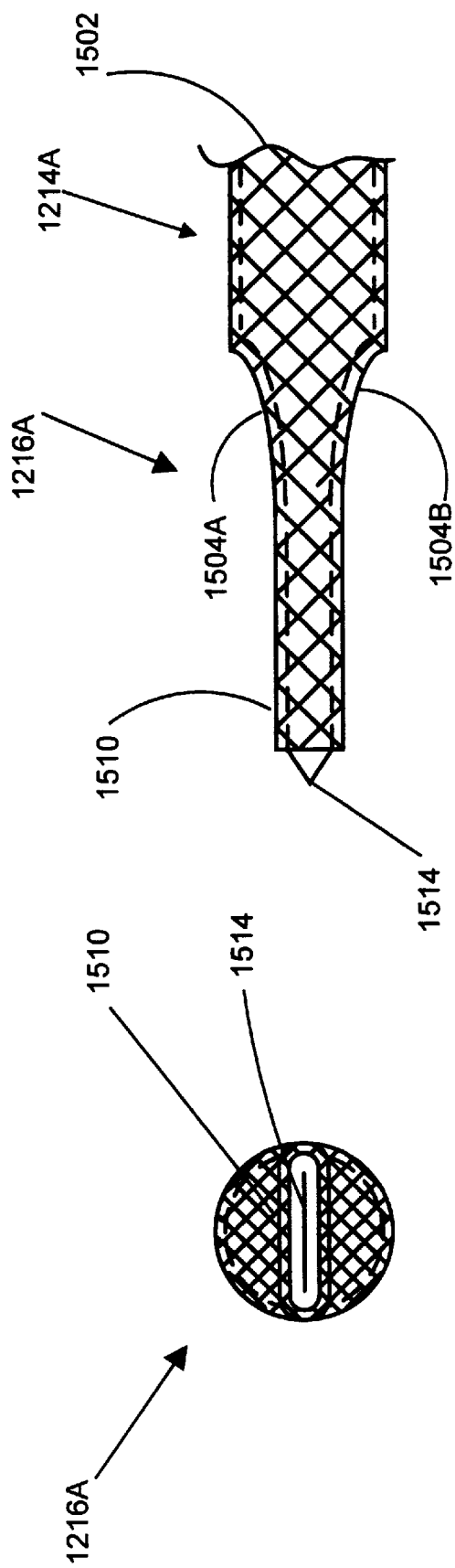
FIG. 15 illustrates an alternate embodiment of a probe with cutting tip.

FIGS. 15A–B show an enlarged view of one embodiment of the tip 1510 of an electrosurgical instrument wherein two opposing arcuate segments 1504A and 1504B are compressed to form a probe tip 1216A at the distal end of probe 1214A. In such an embodiment, swagging is used to compress the tip of the probe. Swagging forms a chisel 1514 that can be used in the surgical instrument of FIGS. 12 and 13 for RF ablation of tissue. Grinding applications can be added to the tip to provide for mechanical tissue ablation in addition to energy ablation. The core 1502 of probe 1214A can be either hollow or solid. This particular embodiment is illustrated as having an annular probe. Probe 1214A is coated in an insulating material which terminates prior to the tip 1510, leaving chisel 1514 exposed.

The surgical chisel illustrated in FIGS. 15A–B provides various improvements over the prior art in allowing for precise hemostatic cutting and ablation of soft tissue in one convenient instrument. The malleable probe tips can be configured as straight, angled or curved, for example, which provides for optimal access to specific anatomy and pathology. Unique tip designs improve tactile feedback for optimal control and access, and provide for improved tissue visualization with greatly reduced bubbling or charring.

EXAMPLES

Example 1

Lateral retinacular release as mentioned above can be accomplished with the use of the concave-tipped RF probe as shown in FIG. 3. First, the knee joint is distended with a clear fluid, usually saline. Initial distention can be done using a large syringe full of saline which is injected into the joint space. Distention forces the bones of the joint apart creating room to introduce instrumentation without damaging the cartilage.

Once the instrumentation has been inserted into the joint space, the irrigation tubing and cannulas are positioned and hooked up to provide continual fluid exchange during the procedure. The most common systems are gravity flow or the use of an arthroscopic irrigation pump. Just hanging bags of irrigation fluid on an IV pole raises them 3–4 feet above the operative site. This elevation difference is enough to create pressure to distend and irrigate the joint. The fluid enters the joint through the scope sheath and exits through a cannula placed in the superior lateral portal, or the reverse, through the cannula and out through the scope sheath. The setup is a matter of physician preference. The key to the proper function of either system is that the inflow volume must be larger than the outflow volume. This restriction in the outflow is what creates the back flow that distends the joint.

With an arthroscopic irrigation pump, the bags do not need to be raised on an IV pole. The factors controlling distention of the joint are controlled automatically by the pump. The pump monitors the fluid pressure in the joint space using a pressure sensing cannula and automatically increases or decreases fluid flow as needed to provide optimum viewing. As with the gravity flow system, fluid enters the joint cavity through the scope sheath or the cannula in the superior lateral portal.

Such an arthroscopic procedure requires the creation of two to five portals (entry ways) into the joint capsule. To create a portal, the surgeon usually begins by making a small stab wound with a scalpel (e.g., No. 11 blade) at the site of the portal. Next, the wound is enlarged and extended with a trocar encased in a sleeve (cannula) through muscle tissue to the synovial membrane. The trocar is removed, leaving the cannula in place. Then, the surgeon uses a blunt obturator (to avoid damage to meniscus and articular cartilage) to puncture through the synovium into the joint cavity. The obturator is removed and the cannula left in place. The cannula can be used to insert an arthroscope or for the inflow and outflow of water. If the surgeon elects to insert instruments percutaneously, the sleeve is removed.

For lateral retinacular release, the surgeon frequently uses three portals, one for the arthroscope, one for the instrument and one for the drain. Additional portals may be created for the surgeon to access other areas of the knee (i.e., to tighten the medial retinaculum) during the procedure. Frequently, a superolateral (above and to the side of the patella) approach is used for the irrigation cannula. For the arthroscope and concave probe, anteromedial and anterolateral approaches often are chosen, because they are relatively safe (minimal potential tissue damage) and most surgeons have more experience with them. Once the arthroscope is viewed, the surgeon may use the concave-tipped probe (without power) to advance to the site of the lateral retinaculum. Having located the lateral retinaculum, the surgeon actuates the RF probe and cuts entirely through the ligament.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

All publications and patent applications mentioned in this specification are herein incorporated by reference to the same extent as if each individual publication or patent application was specifically and individually indicated to be incorporated by reference.

What is claimed is:

1. A method of cutting a ligament or tendon, comprising:
   providing an RF probe with a distal tip having a concave curve located between a pair of lateral edges;
   moving the RF probe to the ligament or tendon to be cut;
   constraining tissue with the concave curve; and
   applying RF energy through the concave curve, thereby cutting the ligament or tendon.

2. The method of claim 1, wherein providing the RF probe includes providing the RF probe with:
   a proximal end; and
   a cabling coupled to a proximal end of the RF probe.

3. The method of claim 2, wherein providing the RF probe includes providing a sharp edge on the concave curve.

4. The method of claim 1, wherein providing the RF probe includes providing a sharp edge on the concave curve.

* * * * *

UNITED STATES PATENT AND TRADEMARK OFFICE
CERTIFICATE OF CORRECTION

PATENT NO. : 6,135,999
DATED : October 24, 2000
INVENTOR(S) : GARY S. FANTON et al.

It is certified that error appears in the above-identified patent and that said Letters Patent is hereby corrected as shown below:

ON THE TITLE PAGE

Item [73] Assignee should read -- ORATEC Interventions, Inc. --.

Signed and Sealed this

Eighth Day of May, 2001

Attest:

NICHOLAS P. GODICI

*Attesting Officer*     *Acting Director of the United States Patent and Trademark Office*